United States Patent [19]

LaNoue et al.

[11] Patent Number: 6,060,481
[45] Date of Patent: May 9, 2000

[54] METHOD FOR IMPROVING INSULIN SENSITIVITY USING AN ADENOSINE RECEPTOR ANTAGONIST

[75] Inventors: Kathryn F. LaNoue, Hershey; George H. Crist, Harrisburg, both of Pa.; Joel M. Linden, Charlottesville, Va.

[73] Assignee: The Penn State Research Foundation, University Park, Pa.

[21] Appl. No.: 09/259,201

[22] Filed: Mar. 1, 1999

Related U.S. Application Data

[63] Continuation-in-part of application No. 09/086,101, May 28, 1998, abandoned.

[51] Int. Cl.$^7$ .................................................. A61K 31/52
[52] U.S. Cl. ............................................... 514/263
[58] Field of Search ............................................. 514/263

[56] References Cited

U.S. PATENT DOCUMENTS

| | | |
|---|---|---|
| 5,204,346 | 4/1993 | Shiokawa et al. . |
| 5,208,240 | 5/1993 | Peet et al. . |
| 5,270,311 | 12/1993 | Caulkett et al. . |
| 5,300,298 | 4/1994 | LaNoue . |
| 5,446,046 | 8/1995 | Belardinelli et al. . |
| 5,547,942 | 8/1996 | Rapaport ..................................... 514/47 |
| 5,631,260 | 5/1997 | Belardinelli et al. .................... 514/263 |
| 5,668,139 | 9/1997 | Belardinelli et al. .................... 516/263 |

OTHER PUBLICATIONS

Feoktistov and Biaggioni, Adenosine $A_{2B}$ Receptors, Pharmacological Reviews, 1997, pp. 381–402, vol. 49, No. 4, The American Society for Pharmacology and Experimental Therapeutics, USA.

Xu et al., $A_1$ adenosine receptor antagonism improves glucose tolerance in Zucker rats, American Journal of Physiology, (1998) pp. E271–E279, vol. 24, American Physiological Society.

*Primary Examiner*—James H. Reamer
*Attorney, Agent, or Firm*—Thomas J. Monahan

[57] ABSTRACT

Methods for improving insulin sensitivity in a patient using one or more $A_{2B}$ adenosine receptor antagonists are disclosed. These methods stimulate insulin dependent glucose uptake in muscle.

15 Claims, 10 Drawing Sheets

METHOD FOR IMPROVING INSULIN SENSITIVITY USING AN ADENOSINE RECEPTOR ANTAGONIST

CROSS REFERENCE TO RELATED APPLICATION

This is a continuation-in-part of application Ser. No. 09/086,101 filed on May 18, 1998 now abandoned.

FIELD OF THE INVENTION

The present invention is directed to methods for improving insulin sensitivity in a patient. The methods find application, for example, in the treatment of non-insulin dependent diabetes mellitus and impaired glucose tolerance. The present methods generally comprise administration of a composition comprising at least one adenosine receptor antagonist to the patient being treated.

BACKGROUND OF THE INVENTION

Diabetes mellitus is a disease in which the body's metabolism of sugars is greatly impaired due to either the faulty secretion of insulin by the pancreas or the body's inability to properly use the insulin. Insulin is a hormone that regulates the level of blood glucose, and controls the rate at which glucose is transported into fat and muscle cells. In addition, insulin regulates numerous anabolic processes in a variety of other cell types. When excess glucose is transported into fat cells it is converted to triglycerides which are stored as energy reserves and, eventually, when the stores are needed and insulin is low, the triglycerides are broken down into fatty acids which are either released or converted by the liver into ketones. Insulin actively inhibits breakdown of triglycerides (lyolysis) in fat cells and actively stimulates synthesis of triglycerides from glucose. Therefore when insulin levels are low, triglycerides are broken down and the stored fat is lost. Insulin also stimulates glucose uptake into muscle cells, where the glucose is consumed to produce energy or is converted into glycogen, which is a storage form of glucose. In the liver, glucose transport is not insulin sensitive but conversion of intracellular glucose to glycogen is stimulated by insulin. The liver can convert amino acids to glucose; this process is inhibited by insulin. Binding of insulin by tissue cells depends on insulin receptors on the surface of insulin-sensitive cells. The receptor/insulin complex which extends across the cell membrane transmits signals to the inside of the cell. These signals increase glucose transport in selected cells and alter cell metabolism in most cells.

Diabetes is characterized by elevated levels of glucose in the blood, which can in turn lead to high glucose levels in the urine. Four types of diabetes mellitus have been clinically observed: non-insulin dependent diabetes mellitus (NIDDM); insulin-dependent diabetes mellitus (IDDM); gestational diabetes mellitus (GDM); and diabetes secondary to other conditions. The total incidence of diabetes in the United States population in 1993 was 3.1%, a 500% increase over the incidence of diabetes in 1958. See M. I. Harris, *Classification, Diagnostic Criteria, and Screening for Diabetes*, In: *Diabetes in America* (National Institutes of Health, Second Ed. 1995).

IDDM, GDM and secondary diabetes constitute a small portion of the diabetes problem in the United States. Insulin-dependent diabetes is typically manifest as a lack of physiologically functional insulin. IDDM cases typically occur at an early age as a result of autoimmune destruction of the pancreatic β-cells, which are responsible for insulin production. IDDM can also result from cytotoxic destruction of the pancreas, or from errors in insulin synthesis and processing. The most debilitating of diabetic conditions, IDDM fortunately only constitutes approximately 5% of known cases in the United States. Gestational diabetes mellitus is observed in 3%–5% of all pregnancies and typically disappears postpartum. GDM is usually manageable through dietary alterations alone. Diabetes secondary to other conditions (such as sepsis) represents a minor component (1%–2%) of the total cases encountered, but can be serious since it manifests in individuals whose health is already compromised.

The vast majority of diabetics are diagnosed with NIDDM, also commonly referred to as "type II" or "adult-onset" diabetes. In the United States, the incidence of NIDDM is rising sharply. Of the 7.8 million people characterized as diabetic in the United States in 1993, 90%–95% were considered to be non-insulin dependent diabetics. According to the National Institutes of Health, the prevalence of NIDDM in the United States population was 6.2% of people 45–64 years of age, and 10.4% of people greater than age 64. However, independent public health surveys indicate that these numbers are greatly underestimated. In addition, impaired glucose tolerance, an intermediate state between normal and diabetic, is manifest in 42% of people ages 65–74.

The etiology of NIDDM is heterologous. Several genetic syndromes have been associated with the disease. Usually NIDDM is associated with hyperinsulinemia, or excess insulin, rather than a deficiency of insulin. Insulin receptors do not respond to normal levels of insulin, thereby requiring the pancreas to produce greater quantities of insulin. Eventually the pancreas is unable to meet the demand for insulin. Risk factors for NIDDM include older age, family history of diabetes, minority ethnicity, and obesity. Intraabdominal obesity, long duration of obesity, physical inactivity, and morbid obesity, in particular, predispose one to NIDDM.

Chronic hyperglycemia and hyperinsulinemia observed in NIDDM are associated with a large number of health complications. In 1986, NIDDM-related deaths accounted for approximately 17% of all deaths in the United States for people over age twenty-five. In particular, cardiovascular disease secondary to NIDDM was responsible for over half of these deaths.

The complications that arise due to diabetes adversely affect the quality of life of those who suffer from it and result in significant health care costs. General disability affects over 50% of diabetics. Health care services are provided to diabetics with much greater frequency than to age-matched non-diabetics. Vision disorders, especially diabetic retinopathy, afflict over 20% of NIDDM patients. Some form of neuropathy, kidney disease, vascular disease, or cardiovascular disease eventually affects nearly all diabetics. Diabetes patients comprise 35% of all new cases of end stage renal disease. The annual cost of treating diabetes-associated renal disease in the United States exceeds two billion dollars.

Adenosine is an extracellular messenger generated by all cells in the body. Adenosine, substances that mimic the actions of adenosine, and substances that antagonize the actions of adenosine have important clinical applications. Adenosine regulates a wide array of physiological functions, but its effect in any given cell depends on the type or subtype of adenosine receptor expressed on the surface of that cell.

The effects of adenosine are mediated by four adenosine receptor subtypes, $A_1$, $A_{2A}$, $A_{2B}$, and $A_3$. The expression of adenosine receptor subtypes differs from tissue to tissue, and adenosine is thereby able to modulate a variety of physiological effects in a tissue-specific manner. The four known adenosine receptor subtypes interact with GTP-binding proteins (G-proteins) to mediate their effects. Each of the subtypes interacts with a distinct set of G-proteins, and differs in its affinity for different adenosine receptor agonists and antagonists. In addition, a compound can be an agonist or antagonist for more than one of the receptor subtypes; for example, some compounds such as caffeine and theophylline antagonize all four subtypes. The $A_1$ and $A_3$ adenosine receptors have been shown to interact primarily with inhibitory G-proteins ($G_i$), which act to inhibit adenylate cyclase and reduce intracellular CAMP. The $A_{2A}$ receptor has been shown to elicit an opposite effect, acting through stimulatory G-proteins ($G_s$), to increase adenylate cyclase activity and increase CAMP. The $A_{2B}$ adenosine receptor is believed to signal similarly through $G_s$ (like the $A_{2A}$ receptor), but may also signal through another class of G-proteins ($G_q$) to increase phospholipase C activity, and subsequently, protein kinase C activity. Protein kinase C influences cell metabolism by phosphorylating enzymes and other cell proteins.

Numerous compounds have been reported as functioning as adenosine receptor antagonists; numerous uses for these compounds have also been reported. For example, U.S. Pat. Nos. 5,446,046, 5,631,260 and 5,668,139 disclose adenosine and/or xanthine derivatives that function in either the agonism or antagonism of $A_1$ receptors. Use of these compounds to modulate the biological activity of adenosine through the $A_1$ receptor, particularly in the treatment of cardiac arrhythmias, is also disclosed.

Xu et al., reported the use of a xanthine derivative, particularly 1,3-dipropyl-8-(p-acrylic)-phenylxanthine, as an $A_1$ adenosine receptor antagonist that improves glucose tolerance in Zucker rats. *American Journal of Physiology*, 24:E271–E279 (1998).

Because of the potentially significant health risks associated with decreased insulin sensitivity which accompanies NIDDM, there remains a need for improved methods for increasing insulin sensitivity in patients with this and related diseases.

SUMMARY OF THE INVENTION

The present invention has met the above described need by providing methods for improving insulin sensitivity in a patient. The methods generally include administering to a patient an effective amount of a composition comprising at least one $A_{2B}$ adenosine receptor antagonist. Any $A_{2B}$ adenosine receptor antagonist can be used in the present method. Relatively water soluble compounds are preferred.

In other embodiments, methods for stimulating glucose transport into muscle and reducing tyrosine phosphatase levels in muscle cells are disclosed; these methods also comprise administering to a patient an effective amount of at least one $A_{2B}$ adenosine receptor antagonist.

Administration of adenosine receptor antagonist compositions according to the present invention can be by any method of introduction known in the pharmaceutical arts. For example, compounds can be introduced systemically, such as by oral administration, intravenous administration, cutaneous or sub-cutaneous injection, or intrathecal injection. These compounds can also be administered by direct application to a mucous membrane.

It is therefore an object of the present invention to provide methods far improving insulin sensitivity in a patient.

A further object of the invention is to provide methods for alleviating at least one of the symptoms of glucose intolerance in diabetic and pre-diabetic patients.

A further object of the invention is to provide tissue-specific means for increasing insulin sensitivity.

A further object of the invention is to provide a method for stimulating uptake of glucose in muscle cells.

These and other objects of the invention will be apparent to those skilled in the art.

DESCRIPTION OF THE INVENTION

Figure 1A:
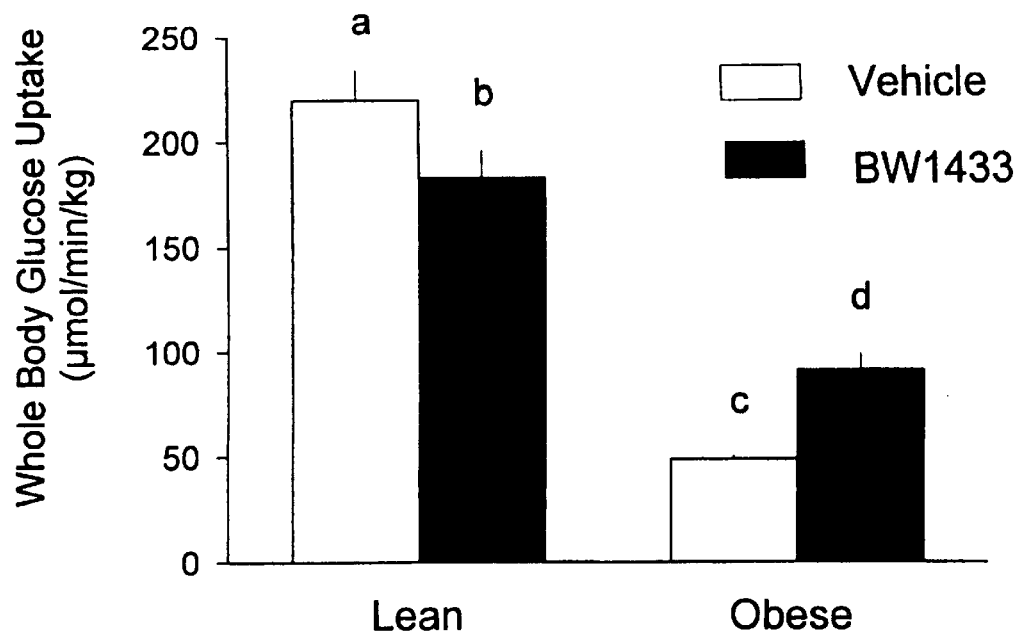
FIG. 1 shows two graphs measuring whole body glucose uptake (top) and insulin-mediated glucose uptake (bottom), determined according to the methods of Example 2.

The present invention provides methods for improving insulin sensitivity in a patient comprising administering to said patient an effective amount of at least one $A_{2B}$ adenosine receptor antagonist, or a pharmaceutically acceptable salt or solvate thereof. "Patient" as used herein refers to members of the animal kingdom, including but not limited to humans.

The methods of the present invention find particular application in the treatment of patients having insulin resistance or insulin insensitivity. The terms "insulin resistance" and "insulin insensitivity" as used herein refer to impairment of the body's ability to use insulin. Symptoms normally associated with insulin insensitivity include high ratios of serum insulin to serum glucose. As the ability to use insulin diminishes, blood glucose levels are severely elevated. This condition is termed hyperglycemia; as a result, glucose may appear in the urine. Insulin insensitivity also leads to kidney failure, cardiovascular disease and vision impairment. The methods of the present invention have as their objective the reversal, at least in part, of insulin insensitivity; this reversal results in the delay, if not the prevention, of the sequelae of hyperglycemia. "Improving insulin sensitivity" therefore refers to any degree in improvement of the symptoms of insulin insensitivity. Thus, the effect of the present methods is to aid in normalizing blood glucose levels and insulin resistance; normalization of these parameters helps to retard the onset, if not prevent, the complications of diabetes. In those patients who are pre-diabetic, the methods of the present invention serve to normalize blood insulin levels, and can retard the onset of, or prevent, full-blown diabetes. "Pre-diabetic" refers to patients who are in the early stages of NIDDM.

The patients benefitting most from the present invention will include, for example, those having NIDDM and those who are pre-diabetic; in addition, any patient showing impaired glucose tolerance or high fasting insulin levels relative to blood glucose will benefit. A patient having impaired glucose tolerance typically has had an abnormal glucose tolerance test, but has a fasting blood glucose level that is either normal or only slightly elevated. This condition is also known as asymptomatic diabetes, chemical diabetes, borderline diabetes or latent diabetes.

As noted above, binding insulin to insulin receptors on the cell surfacer stimulates muscle cells to take up glucose. The receptor spans the membrane and insulin binds from outside. Upon binding, insulin changes the shape of the insulin receptor, turning it into an enzyme that phosphorylates tyrosine residues on the receptor itself (autophosphorylation) and on other proteins. It is this phosphokinase activity that is responsible for the actions of insulin. Since the insulin receptor does not possess the ability to terminate its own activity once autophosphorylated, protein tyrosine phosphatases (PTPases) are required for the termination of signals involving tyrosine kinases. LAR and PTPase 1B are PTPases that have been shown to attenuate insulin receptor kinase activity. In general, phosphatase activity is higher in the skeletal muscle plasma membrane-enriched fractions than in cytosolic fractions. Recent investigations show that tyrosine phosphatase activity is elevated in muscle biopsies of NIDDM patients and in rats with genetically inherited NIDDM. High levels of tyrosine phosphatases may prevent the insulin receptors from influencing metabolism. The methods of the present invention also serve to lower the levels of tyrosine phosphatases in insulin insensitive patients, which may allow for more active functioning of the insulin receptors.

The present methods improve insulin sensitivity through the administration to a patient of at least one $A_{2B}$ adenosine receptor antagonist, or a pharmaceutically acceptable salt or solvate thereof. Targeting of the $A_{2B}$ receptors as taught herein provides significant advantages over other methods in the art, which utilize exercise, diet and/or drugs that increase insulin secretion. Rather than increasing insulin secretion, the present methods result in increased insulin sensitivity in muscle; insulin sensitivity in adipose or fat tissue either decreases or remains unchanged. This provides a distinct advantage over other treatments in that it increases the effectiveness of insulin; glucose is directed to muscle where it is burned for energy and away from adipose tissue, where it may be stored as triglyceride (fat). Excess fat storage constitutes a health risk by worsening insulin resistance and increasing the likelihood of cardiovascular disease. Adenosine $A_{2B}$ receptors are found in muscle tissue but not in adipose tissue. Because the compounds used in the methods of the present invention target and antagonize the $A_{2B}$ receptor, glucose uptake is stimulated in muscle; because the $A_{2B}$ receptors are not found at significant levels in adipose tissue, the compounds used in the present invention do not stimulate glucose uptake in that tissue. The present invention therefore provides an advantage over typical methods currently employed in the art that seek to stimulate glucose uptake in fat tissue.

Any $A_{2B}$ adenosine receptor antagonist can be used according to the present methods. Methods for determining whether a compound is an $A_{2B}$ adenosine receptor agonist or antagonist involve quantitating its binding affinity to membranes which are known to contain the $A_{2B}$ subtype. The methods for determining whether compounds are specific ligands of different adenosine receptor subtypes will be known by practitioners of the art. For example, a review article by Feoktistov and Baggioni, (*Pharmacological Reviews* 49, 381–402 (1997)) reports the binding affinity of eight adenosine receptor agonists and eight antagonists for all four subtypes of adenosine receptors. References cited therein provide more complete descriptions of the procedures used. (Robeva A. S., Woodward R. L., Jin X. and Gao Z., Linden J. *Drug Dev. Res* 39:243–252 (1996); Jacobson K. A. and Suzuki F. *Drug Dev. Res.* 39, 289–300, (1996); Feoktistov, I. and Baggioni, I. *Molecular Pharmacology* 43, 909–914 (1993)). Effective methods for determining the binding affinity of a compound for a receptor use a radio-labelled agonist or antagonist and correlation of the binding of that compound to a membrane fraction known to contain that receptor; for example, to determine whether a compound is an $A_{2B}$ antagonist, the membrane fraction would contain the $A_{2B}$ adenosine receptor. Another particularly effective procedure for determining whether a compound is an $A_{2B}$ antagonist is reported in Ser. No. 08/670,175, which is hereby incorporated by reference. Basically, this method involves determining the concentration of a test compound required to half-maximally inhibit the binding of a radioligand, 125I-ABOPX, (3-(3-125iodo4-aminobenzyl)-8-phenyloxyacetate-1-propyl-xanthine), to recombinant human adenosine receptors.

Compounds selective for the $A_{2B}$ receptor subtype are therefore preferred for the present methods. An example, but not a limitation, of such a compound is 3-n-propylxanthine (enprofylline). Other examples include 1,3-dimethylcyclohexyl-8-phenyl(4acrylate)-xanthine and other compounds with variations in the 1, 3 and/or 8 positions of the xanthine ring, such as those discussed in U.S. Ser. No. 09/1027,649, which is hereby incorporated by reference. Compounds which antagonize other receptors in addition to the $A_{2B}$ receptor are also be within the present invention. One example of such a compound is 1,3-dipropyl-8-(p-acrylic)phenylxanthine (BWA1433). The binding constants ($K_D$) of enprofylline and BWA1433 are shown below in Table I.

TABLE I

Binding constants ($K_D$) of two adenosine receptor antagonists as measured against cloned and expressed human adenosine receptor subtypes. Values shown are nM.

|  | $A_1$ | $A_{2A}$ | $A_{2B}$ | $A_3$ |
|---|---|---|---|---|
| BWA1433 | 140 | 190 | 60 | 30 |
| Enprofylline | 156,000 | 32,000 | 7,000 | 65,000 |

Enprofylline's low $K_D$ for $A_{2B}$, relative to the other subtypes, demonstrates its selectivity as an $A_{2B}$ antagonist. The values shown for BWA1433 demonstrate that BWA1433 is an antagonist of $A_{2B}$ receptors, as well as others. It should be noted that the rat $A_3$ receptor has a much higher $K_D$ for BWA1433 than does the human $A_3$ receptor, and that the effect of $A_{2A}$ receptors on muscle insulin sensitivity has been previously ruled out (Challiss, R. A., Richards, S. J., Budohoski, L. Eur. *J. Pharmacol.* 226:121–128 (1992)). Moreover the $K_D$ for the rat $A_3$ receptor is much higher than for the human $A_3$ receptor (Wang, J., Drake, L., Sajjadi, F., Firestone, G. S., Mullane, K. M. and Bullough, D. A. *European Journal of Pharmacology*, 320:241–248 (1997)). Studies of the distribution of adenosine receptors in various rat tissues show that there is no $A_1$ adenosine receptor nor any $A_3$ adenosine receptor mRNA in muscle, as assessed by the very sensitive PCR technique. (Dixon, A. K., Gubitz, A. K., Sirinathsinghui, D. J., Richardson, D. J., and Freeman, T. C. *British Journal of Pharmacology*, 118:1461–1468 (1996)). Thus, as determined by the present inventors, the influence of BWA1433 and other drugs on muscle insulin sensitivity is exerted via the $A_{2B}$ adenosine receptor. $A_1$ adenosine receptors transduce their effect when activated through the GTP binding protein $G_1$, whereas the $A_{2B}$ influence is transduced by either $G_s$ or $G_q$. $G_q$ stimulates phospholipase C which in turn stimulates protein kinase C. Protein kinase C is known to block insulin action. It has been speculated that protein kinase C may block insulin receptor tyrosine kinase activity by activating protein tyrosine phosphatases. Targeting $A_{2B}$ adenosine receptors by use of $A_{2B}$ adenosine receptor antagonists, as taught herein, is therefore an effective method for improving insulin insensitivity in a patient, through stimulation of glucose uptake in the patient's muscle tissue.

As noted above, particularly preferred for the present methods are $A_{2B}$ adenosine receptor antagonists that are selective for the $A_{2B}$ adenosine receptor versus the other adenosine receptor subtypes. Compounds selective for the $A_{2B}$ receptor, therefore, will function to antagonize the action of $A_{2B}$ receptors, while minimally influencing the activity of other adenosine receptors. Any compound that exhibits $A_{2B}$ adenosine receptor antagonism, regardless of specificity, is within the scope of the present invention, however. One class of compounds which provides potential $A_{2B}$ adenosine receptor antagonists are xanthine derivatives. As used herein, the term "xanthine derivative" refers to a compound having a xanthine core to which is attached any number of additional groups. Examples include but are not limited to enprofylline, BWA1433, 1,3-dipropyl-8-cyclopentylxanthine (DPCPX), 1,3-dipropyl-8-(p-sulfophenyl)xanthine (DPSPX), xanthine amine congener (XAC), and 1,3-dipropyl-8,-[2-(5,6-epoxynorbonyl] xanthine; those skilled in the art will appreciate that these compounds are xanthine molecules to which are covalently attached various substituents. Such compounds are described, for example, in U.S. Pat. No. 5,446,046. The '046 patent also describes oxatricycloalkylxanthines, the use of which is also within the scope of the present invention to the extent that the compounds are antagonists of the $A_{2B}$ receptor. In addition, U.S. Pat. No. 5,300,298 describes purine derivatives which can be used according to the methods of the present invention. The '298 patent is hereby incorporated by reference.

Compounds which function as $A_2$ adenosine receptor antagonists are also reported in U.S. Pat. No. 4,772,607; quinoxaline derivatives are taught as having excellent binding affinity at both the $A_1$ and $A_2$ adenosine receptor sites in U.S. Pat. No. 4,780,464. U.S. Pat. No. 4,612,315 teaches biologically active 1,3-dipropyl-8-phenylxanthine derivatives that are highly potent and selective antagonists for $A_1$ adenosine receptors. Similar compounds are described in U.S. Pat. No. 4,696,932. Additional xanthine derivatives that function as adenosine receptor antagonists are reported in U.S. Pat. Nos. 5,047,534; 5,064,947; 5,066,655; 5,219,839; 5,229,505; 5,329,007; 5,342,841; 5,380,714; 5,430,027; 5,453,426; 5,670,498; 5,670,501; 5,756,735 and 4,755,517. The above references appear to teach compounds that are both $A_1$ and $A_2$ adenosine receptor antagonists, and do not differentiate between $A_{2A}$ and $A_{2B}$ adenosine receptor antagonists. Additional adenosine receptor antagonists are reported in U.S. Pat. Nos. 4,593,095; 5,204,346; 5,208,240; 5,273,311; 5,326,869; 5,356,894; 5,378,844; 5,391,739; 5,395,836; 5,432,164; 5,500,428; 5,504,090; 5,565,566; 5,641,784; 5,688,802; and 5,773,530. Compounds disclosed in any of the above patents may prove suitable for the methods of the present invention by selectively, or relatively selectively, antagonizing the $A_{2B}$ adenosine receptor; as discussed above, the determination as to whether a compound is an $A_{2B}$ adenosine receptor antagonist can be determined by those skilled in the art based upon the teachings of, for example, Feoktistov and Biaggioni (1997) or U.S. Ser. No. 08/670,175. Generally, therefore, compounds that are potential candidates for $A_{2B}$ adenosine receptor antagonism are xanthines, pyridines, purines, theophyllines, triazines, quinazolines, alkyl adenosines, and derivatives of all of these compounds.

As discussed above, it is also preferred that the $A_{2B}$ adenosine receptor antagonist compound be relatively water soluble. This is to ensure that the concentration of the compound present in the blood stream will be sufficient to bind with enough $A_{2B}$ adenosine receptors to produce the desired result. As an example, compounds having polar substituents, acidic functional groups, and the like will typically have an appropriate water solubility for use in the present methods.

While it is possible for the compounds used in the methods of the present invention to be administered to a patient as the raw chemical, it is preferred to present them in the form of a pharmaceutical formulation and with appropriate carriers as the use may require. Accordingly, in the present methods, pharmaceutical formulations may be utilized which comprise at least one $A_{2B}$ adenosine receptor antagonist, or a pharmaceutically acceptable salt or solvate thereof, and a suitable pharmaceutically acceptable carrier therefor. The expression "suitable pharmaceutical carrier" as used herein refers to carriers that are compatible with the $A_{2B}$ adenosine receptor antagonist being employed by the user, and which are not detrimental to the patient. The carrier itself may constitute one or more excipients conventionally used in the art of pharmacy that enable compounds to be formulated as a pharmaceutical preparation suitable for administration to a patient. Examples include but are not limited to liquid carriers and solid carriers.

The pharmaceutical formulations of the present invention include those suitable for oral, parenteral (including subcutaneous, intradermal, intramuscular and intravenous) and rectal administration although the most suitable route will probably depend upon, for example, the precise nature and severity of the insulin insensitivity and the patient being treated. The formulations may conveniently be presented in unit dosage form and may be prepared by any of the methods well known in the art of pharmacy. These methods include the step of bringing into association the active ingredient, here at least one $A_{2B}$ adenosine receptor antagonist, or pharmaceutically acceptable salt or solvate thereof, with a carrier. In general, the formulations are prepared by uniformly and intimately bringing into association the active ingredient with, for example, a liquid carrier, a finely divided solid carrier or both, and then, if necessary, forming the associated mixture into the desired formulation.

Pharmaceutical formulations of the present invention suitable for oral administration may be presented as discrete units, such as capsule, cachet tablet, or lozenge, each containing a predetermined amount of active ingredient as a powder or granules; as a solution or a suspension in an aqueous liquid or a non-aqueous liquid such as syrup, elixir or a draught; or as an oil-in-water liquid emulsion or a water-in-oil liquid emulsion. The formulation may also be a bolus, electuary or paste.

Generally, a tablet is the most convenient pharmaceutical formulation suitable for oral administration. A tablet may be made by compressing or molding. Tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Molded tablets may be prepared by molding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions which may contain, for example, an anti-oxidant, a buffer, a bacteriostat and a solute which renders the composition isotonic with the blood of the recipient, and aqueous and non-aqueous sterile suspensions which may contain, for example, a suspending agent and a thickening agent. The formulations may be presented in unit-dose or multi-dose containers, for example sealed ampoules and vials and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

As noted above, use of $A_{2B}$ adenosine receptor antagonists in their salt and/or solvate form is within the scope of the present invention. Also, more than one $A_{2B}$ adenosine receptor antagonists can be administered according to the methods of the present invention. In addition, at least one $A_{2B}$ adenosine receptor antagonist can be administered to a patient in conjunction with one or more other therapeutic agents, for example, a drug that would also lower serum fatty acid levels.

An effective amount of at least one $A_{2B}$ adenosine receptor antagonist should be administered to the patient. As used herein, the term "effective amount" refers to that amount of $A_{2B}$ adenosine receptor antagonist, or salt/solvent thereof, that is needed to show improved insulin sensitivity of a patient. Improved insulin sensitivity will be manifested by one or more parameters such as improved glucose tolerance, reduced blood glucose levels, reduced urine glucose levels, and in the case of the pre-diabetic subjects, lowered serum insulin levels. An improved glucose tolerance test is a measure of drug effectiveness. Alternatively, an assay of glycosylated hemoglobin in the blood provides a time averaged value for blood glucose over a period of several weeks. Even small improvements in the insulin sensitivity of a patient are within the scope of the present invention.

As with the route of administration, the dosage of the compound given and frequency of the duration will depend on the patient being treated, taking into consideration such factors as the particular insulin insensitivity being treated, the body weight of the patient, other therapies being employed to treat the patient, the clinical response and tolerance of the patient. Dosage, administration, duration and frequency of therapy can be determined by one skilled in the art upon evaluation of these and other relevant factors. The amount used to treat diabetic subjects will depend on the $K_D$ of the particular antagonist used, its route of administration and its serum half life. A minimum dosage will typically be that amount of a compound which will provide a blood concentration in the patient of 10 to 20 times the binding constant of the compound.

EXAMPLES

The following examples are intended to illustrate the invention, and should not be interpreted as limiting the invention in any way.

The examples presented below utilized Zucker rats as an animal model for the study of insulin resistance. Generally, obese, insulin-resistance rodents have proven to be effective animal models in the study of diabetes. Hyperinsulinemia, hyperphagia and obesity are some of the hallmark features of these animals. The genetically obese (fa/fa) Zucker rat is not normally hyperglycemic, but exhibits poor glucose tolerance, insulin resistance. The animal model shares many characteristics in common with human subjects in the early stages of NIDDM. These characteristics include a striking tissue specificity of the insulin resistance. Muscle tissue is insulin resistant while adipose tissue exhibits normal or increased sensitivity to insulin.

Example 1

This example sets forth a procedure for determining whether a compound functions as an $A_{2B}$ adenosine receptor antagonist.

The general method used to determine whether a compound is an effective adenosine $A_{2B}$ receptor antagonist measures the ability of the compound to bind to an authentic $A_{2B}$ receptor incorporated into a cell membrane. This method would be analogous to methods which show that BWA1433 is an effective $A_1$ adenosine receptor antagonist, but utilizing parameters for the $A_{2B}$ receptor rather than an $A_1$ receptor. In these previous methods, a radioactive compound (DPCPX) known to be highly specific for $A_1$ adenosine receptors and whose $K_D$ is published was incubated with isolated fat cell membranes. $A_1$ adenosine receptors are abundant in fat cells and DPCPX's binding to fat cell membranes occurs due to those receptors. As shown in FIG.

1 of Xu et al (1998), BWA1433 competes with $^3$H-DPCPX and from the concentration dependence of BWA1433's ability to remove $^3$H-DPCPX from its binding site on the membrane one can calculate the $K_D$ of BWA1433 for rat $A_1$ adenosine receptors. Human cells which express large amounts of human $A_{2B}$ adenosine receptors are not readily available. Therefore, in order to determine the $K_D$ of BWA1433 for the $A_{2B}$ adenosine receptor the cDNA of human $A_{2B}$ adenosine receptor was used to overexpress the $A_{2B}$ adenosine receptor in a mammalian cell line. Then the concentration dependence of BWA1433 binding to isolated membranes of these cells was determined in a similar way to that shown in FIG. 1 of Xu et al 1998. This method is described fully in U.S. Ser. No. 08/670,175. The binding data obtained which provides the $K_D$'s of BWA1433 for all four subtypes are listed in Table I. The data were obtained by separately overexpressing each adenosine receptor subtype in mammalian cell lines.

Example 2

In this example, 6–8 week old lean and obese female animals were used. Each group received either vehicle or vehicle plus 1,3-dipropyl-8-(p-acrylic)phenylxanthine (BWA1433) (12 mg/kg every 12 h) for one week prior to the start of the experimental protocol, as described by Xu, et al., *Am. J. Physiol.,* 274 (Endocrinol. Metab. 37): E271–E279 (1988). The vehicle in this case was 10 mg/ml methyl cellulose in $H_2O$. The final dose of BWA1433 or vehicle was administered approximately 1 h prior to the start of the experimental protocol.

On the day prior to the start of the experimental protocol, animals were anesthetized with an intramuscular injection of ketamine and xylazine (90 and 9 mg/kg body weight, respectively), and sterile surgery was performed to implant catheters in the carotid artery and jugular vein according to the methods taught by Lang et al., *Endocrinology,* 130: 43–52 (1992). After surgery, animals were housed in individual cages and provided water ad libitum. Animals were fasted overnight.

Basal Glucose Kinetics and Hyperinsulinemic Clamp

The following morning, a primed, constant intravenous infusion of [3-$^3$H]glucose (high-performance liquid chromatography purified; DuPont-New England Nuclear, Boston, Mass.) was initiated to determine basal glucose kinetics. A 7-μCi bolus injection of labeled glucose was administered followed by a continuous infusion at a rate of 0.083 μCi/min for the next 2 h. Arterial blood samples were collected at 100 and 120 min (0.3 ml each) after the start of the tracer infusion. Blood was collected in heparinized syringes, centrifuged, and the plasma glucose concentration and glucose specific activity were determined on each sample.

After samples were obtained for basal metabolic determinations, a euglycemic hyperinsulinemic clamp was performed. Regular human insulin (Eli Lilly, Indianapolis, Ind.) was infused intravenously at a rate of 100 mU·min$^-$$_1$·kg$^{-1}$ for 3 h. This infusion rate has been previously determined to result in steady-state plasma insulin concentrations of approximately 5,000 uU/ml, as reported in Lang, et al., *Endocrinology,* 130:43–52 (1996); Lang, *Am. J. Physiol.,* 263 (Endocrinol. Metab. 26): E703–E711 (1992); and Lang, et al., Metabolism, 39:1096–1107 (1990). This insulin concentration has been previously demonstrated to maximally stimulate glucose disposal by the whole body and skeletal muscles with different fiber type composition. Tritiated glucose was not infused during the hyperinsulinemic clamp, because preliminary studies indicate that this insulin infusion rate completely suppresses endogenous glucose appearance in both obese and lean animals.

Tissue Glucose Uptake

In vivo glucose uptake by individual tissues was determined using [$^{14}$C]-labeled 2-deoxyglucose (2-DG), as described previously in, for example, the Lang references cited above. Tissue-specific glucose uptake was determined between 140 and 180 min after the start of the euglycemic hyperinsulinemic clamp. A tracer amount of 2-DG (8 μCi/rat; Amersham, Arlington Heights, Ill.) was injected intravenously, and tissues obtained 40 min later. Prior to tissue collection, serial arterial blood samples (0.2 ml) were withdrawn into heparinized syringes, plasma deproteinized with perchloric acid and $^{14}$C-radioactivity determined. Thereafter, animals were anesthetized with sodium pentobarbital, exsanguinated, and selected tissues were excised to determine the intracellular accumulation of phosphorylated 2-DG.

During the hyperinsulinemic clamp, blood glucose concentrations were determined at 10-min intervals using the YSI glucose analyzer (Yellow Springs, Ohio). Glucose specific activity was determined on neutralized supernatants of deproteinized plasma as taught by Lang, *Am. J. Physiol,* 263 (Endocrinol. Metab. 26): E703–D711 (1992). Tissue samples (600–900 mg wet wt) were immersed in ice-cold 0.5 N PCA, homogenized, and centrifuged. The concentration of phosphorylated 2-DG in tissues was calculated as the difference between total $^{14}$C-radioactivity of the neutral extract and the $^{14}$C-radioactivity remaining after Somogyi treatment as described in detail by Lang CH, Dobrescu C, and Meszaros K., *Metabolism* 39:1096–1107 (1990).

Rates of whole body glucose appearance (Ra) and disappearance (Rd) are calculated using the steady-state equations of Steele, *Ann. NY Acad. Sci.,* 82:420–430 (1959). The glucose metabolic clearance rate (MCR) is calculated by dividing the glucose Rd by the prevailing glucose concentration. Since the prevailing insulin levels during the hyperinsulinemic clamp completely suppress endogenous glucose production, the rate of whole body glucose disposal equals the exogenous glucose infusion rate. The increment in insulin-stimulated glucose uptake (IMGU) for each animals is calculated by subtracting the basal endogenous glucose Ra from the measured rate of glucose disposal determined during the last 40 min of the clamp. In vivo glucose uptake for each tissue examined is calculated based on the accumulation of phosphorylated 2-DG by a respective tissue, the integrated 2-DG:glucose ratio in the plasma during the 40-min labeling period, and the lumped constant as described by Lang, *Endocrinology,* 128:645–653 (1991).

Figure 1B:
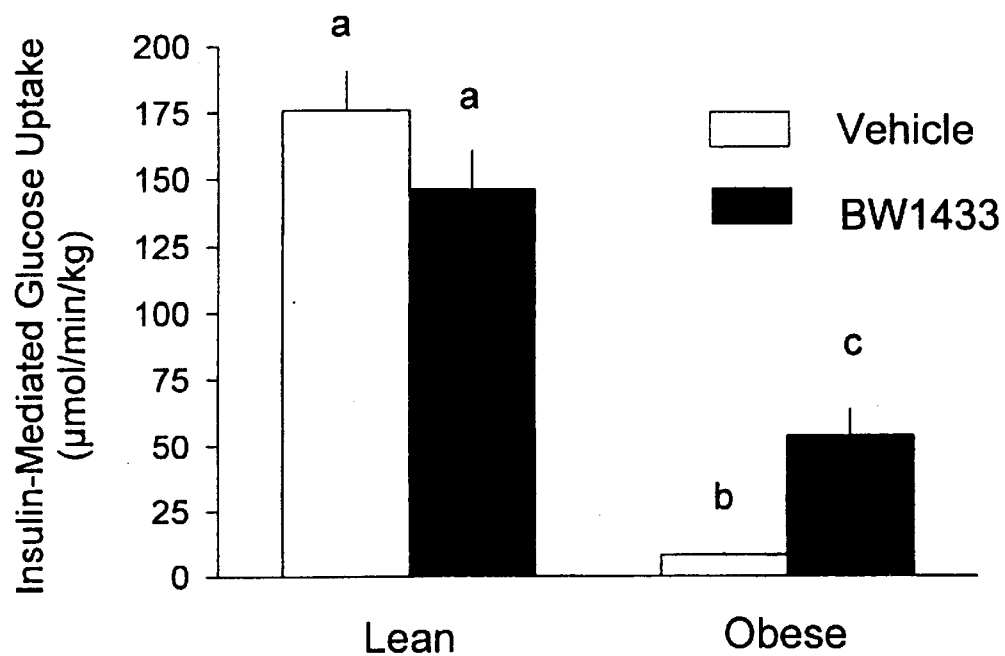
Figure 2A:
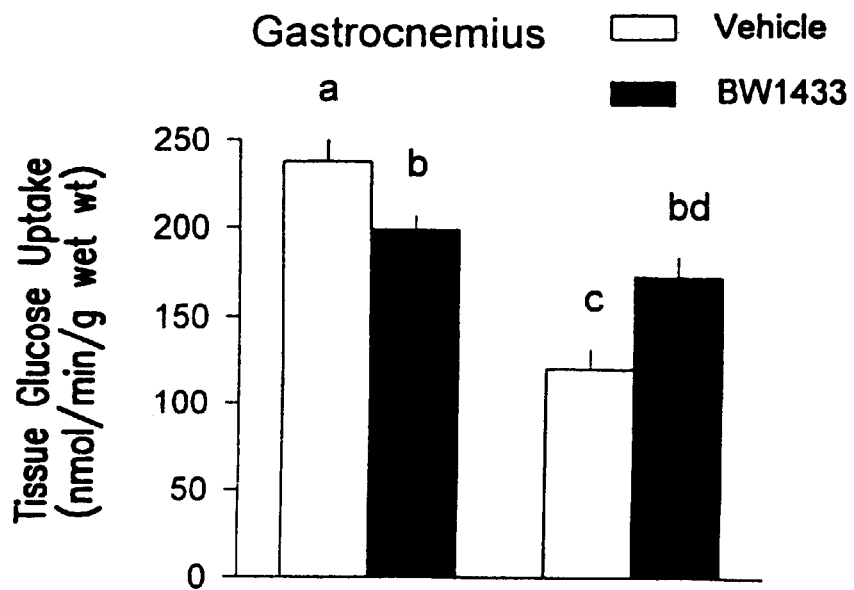
FIG. 2 shows separate graphs for glucose uptake by gastrocnemius, soleus, liver and heart, determined according to the methods of Example 2.
Figure 2B:
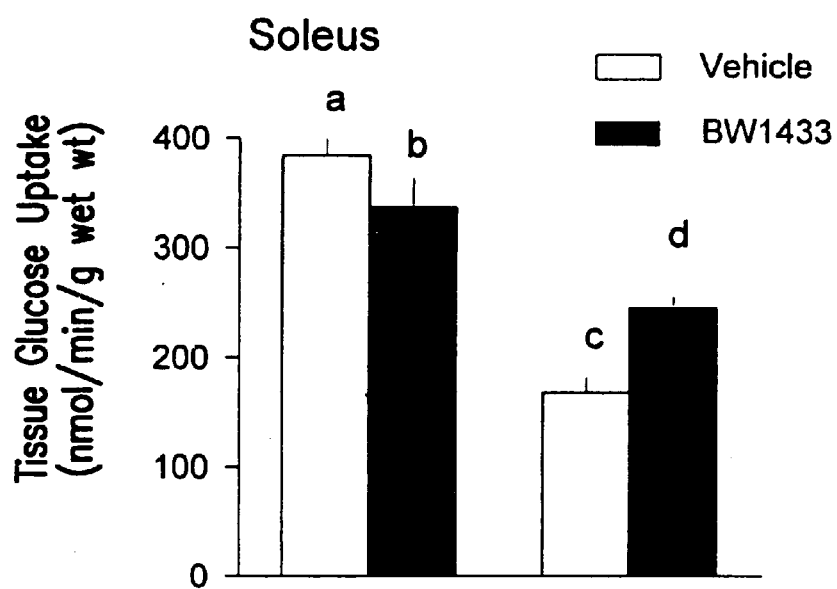
Figure 2C:
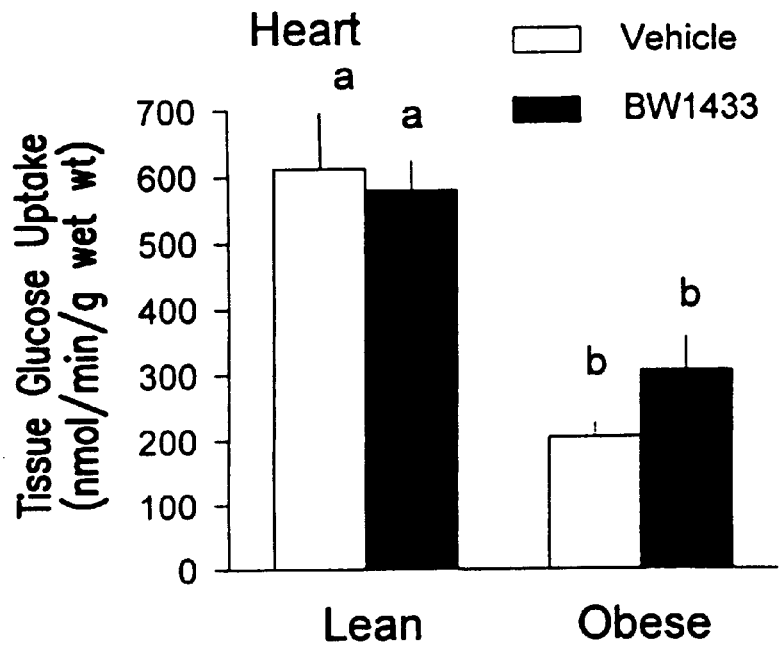
Figure 2D:
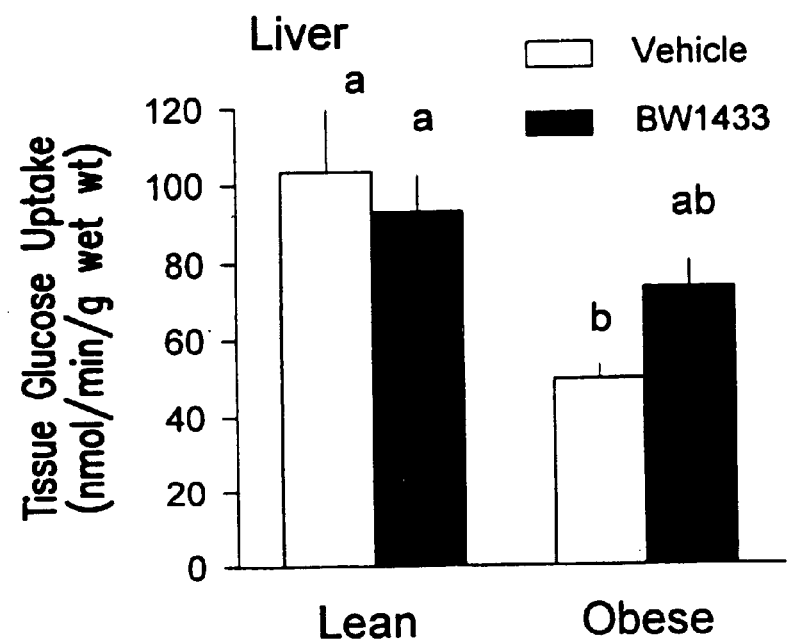
Figure 3A:
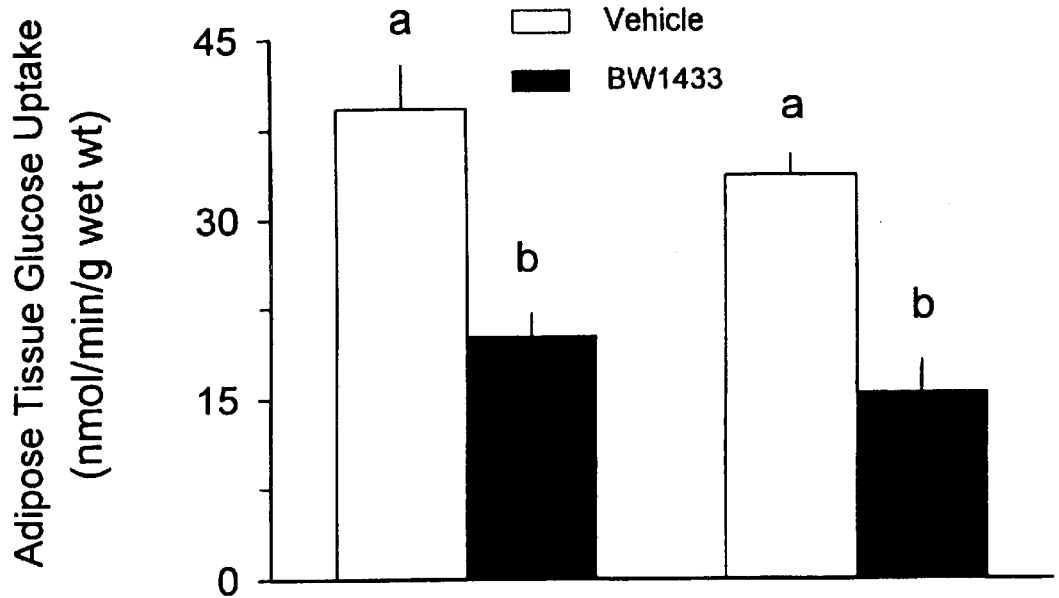
FIG. 3 shows that glucose uptake by adipose tissue was decreased in both NIDDM obese and normal lean rats treated with an $A_{2B}$ adenosine receptor antagonist, determined according to the methods of Example 2.
Figure 3B:
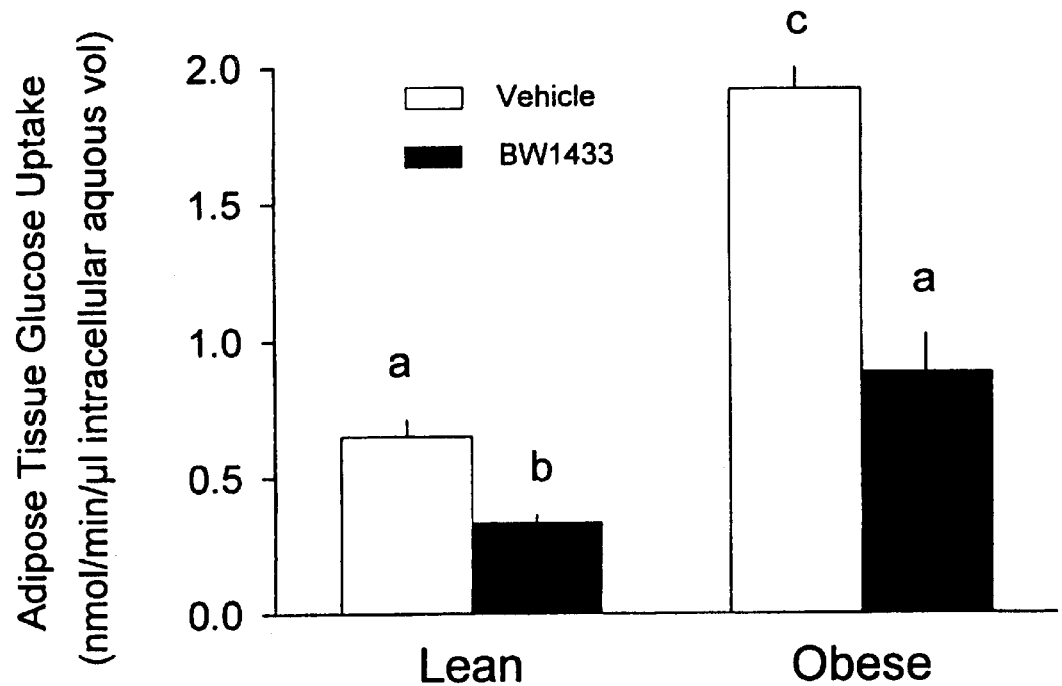

Experimental values are presented as means ± standard error of the mean (SEM). The number of animals per group is indicated in the description of FIGS. 1–3 and Table legends. Data were analyzed using analysis of variance followed by Student-Newman-Keuls test to determine treatment effect. Statistical significance was set at $P<0.05$.

Basal Carbohydrate Metabolism and Whole Body Insulin Action

Treatment of rats with BWA1433 for one week did not produce significant changes in body weight in either the lean or obese animals, as shown in Table II. As expected, the body weight of obese animals was 36% greater than that of their lean litter mate.

The basal postabsorptive arterial glucose concentration, glucose Ra/Rd and MCR did not differ significantly between lean and obese rats (Table II). Moreover, the administration of the adenosine receptor antagonist also did not produce detectable alterations in any parameter of glucose metabolism in either group under basal conditions (Table II).

TABLE II

Basal postabsorptive glucose kinetics in
lean and obese rats treated with BWA1433

|  | Lean Control | Lean BWA1433 | Obese Control | Obese BW1433 |
|---|---|---|---|---|
| Body weight, g | 198 ± 11[a] | 182 ± 5[a] | 256 ± 13[b] | 260 ± 11[b] |
| Glucose Concentration, mM | 5.0 ± 0.3 | 5.1 ± 0.2 | 5.1 ± 0.3 | 4.5 ± 0.2 |
| Glucose Ra, $\mu mol^{-1} \cdot min \cdot kg$ | 43.8 ± 3.6 | 36.8 ± 2.9 | 40.3 ± 1.2 | 37.5 ± 4.8 |
| Glucose MCR, $ml \cdot min^{-1} \cdot kg^{-1}$ | 8.8 ± 0.7 | 7.1 ± 0.8 | 8.0 ± 0.7 | 8.3 ± 0.8 |

Values are means ± SEM; n = 6, 6, 5 and 5, respectively. Both lean and obese animals were treated with vehicle or BWA1433 for 1 wk prior to determinations. Glucose Ra, glucose rate of appearance; Glucose Rd, glucose rate of disappearance; Glucose MCR, metabolic clearance rate of glucose. Under these steady-state conditions, glucose Ra equals the rate of glucose disappearance (Rd). MCR was calculated as the glucose Rd dividend by the prevailing glucose concentrations. Values with different letters are significantly different from each other ($P < 0.05$).

The rate of glucose infusion in each group was stable during the final 60 min of the 3-h euglycemic hyperinsulinemic clamp (data not shown). Furthermore, the average plasma glucose concentration during the final hour of the clamp was not different among the four groups. Glucose concentrations (mM) averaged 5.5±0.1 for lean control, 5.4±0.1 for lean BW1433-treated, 5.6±0.2 for obese control, and 5.5±0.1 for the obese BW1433-treated rats. Plasma insulin concentrations were not determined during the clamp, because previous studies report that the insulin infusion rate used in the current study achieved circulating levels of insulin (i.e., >1000 IU/ml) that are maximally stimulating for glucose uptake. Based on the exogenous glucose infusion rate, whole body glucose disposal in lean control animals was 450% greater than in time-matched obese control rats (FIG. 1, top). Administration of BWA1433 to lean animals resulted in a small (16%) but statistically significant decrease in whole body glucose disposal. In contrast, BWA1433 increased the rate of whole body glucose uptake in obese rats by 88%, compared to values in untreated obese rats. These results are also presented in FIG. 1. Despite the ability of the adenosine receptor antagonist to increase glucose uptake in obese animals, the rate was still approximately 50% lower than that observed in lean control animals.

Under basal conditions, most of the glucose uptake by peripheral tissues occurs via noninsulin-mediated pathways, and the contribution of this non-insulin-mediated glucose uptake (NIMGU) to the overall rate of whole body glucose disposal may obscure changes in IMGU. To account for potential differences in NIMGU among groups, the insulin-dependent increment in glucose disposal was calculated for each animal (FIG. 1, bottom). Whole body IMGU was depressed by 95% in obese control animals, compared to lean controls. Treatment of obese rats with BWA1433 increased IMGU by more than 6-fold, compared to values in vehicle-treated obese animals. No change in IMGU was observed in lean Zucker rats treated with BWA1433.

Tissue Glucose Uptake

Under euglycemic hyperinsulinemic conditions, glucose uptake by gastrocnemius, soleus and heart was lower (50%, 54% and 67%, respectively) in obese control animals, compared to lean control rats, as shown in FIG. 2. Similarly, glucose uptake by whole liver was also lower (52%) in untreated obese animals. One week treatment of obese rats with BWA1433 significantly increased glucose uptake in gastrocnemius and soleus by 44% and 47%, compared to vehicle-treated obese rats. However, there was no significant change in glucose uptake in heart or liver in BWA1433-treated obese rats. The adenosine antagonist also altered insulin-stimulated glucose uptake in lean animals. BWA1433 resulted in a small, albeit statistically significant, decrease in glucose uptake by gastrocnemius and soleus (16% and 12%, respectively) in lean rats. Glucose uptake under hyperinsulinemic conditions was unaffected by BWA1433 in heart and liver of lean animals.

In contradistinction to the response in muscle, glucose uptake by epididymal fat was not significantly different between lean and obese animals, when normalized to wet weight, as shown in FIG. 3, top panel. Furthermore, glucose uptake by adipose tissue was decreased in both obese and lean rats treated with the adenosine antagonist (54% and 48%, respectively). FIG. 3 (bottom panel) illustrates that when calculated on the basis of intracellular aqueous volume, glucose uptake by fat from obese rats was 190%, compared to values from lean animals. Treatment with BWA1433 resulted in an approximately 50% reduction in glucose uptake in both groups of animals; however, the absolute decrease in glucose uptake in fat from obese rats was greater than that observed in lean animals.

These results show that $A_{2B}$ adenosine receptor blockade increases insulin sensitivity. Previous studies have shown that inactivation of the $A_1$ adenosine receptitors decreases rather than increases insulin sensitivity. BWA1433 inactivates both $A_1$ and $A_{2B}$ adenosine receptors with about equal effectiveness (cf Table I for $K_D$'s). Rat adipose tissue has high levels of $A_1$ receptors and few if any $A_{2B}$ receptors, while muscle has no $A_1$ adenosine receptors but detectable levels of $A_{2B}$. The striking difference in the effect of BWA1433 in muscle compared to adipose tissue is best explained by the fact that blockade of $A_{2B}$ increases insulin sensitivity while blockade of $A_1$ adenosine receptors decreases insulin sensitivity. Thus, the methods of the present invention, which use $A_{2B}$ adenosine receptors antagonists, result in increased glucose uptake by muscle, thereby improving insulin sensitivity in a patient. As discussed above, it is in the muscle where glucose is consumed to produce energy is or converted into glycogen.

Example 3

The following example illustrates the use of an $A_{2B}$ adenosine receptor antagonist to lower tyrosine phosphatase levels in muscle tissue. Lowering of the tyrosine phosphatase levels results in improved insulin sensitivity, because the insulin receptor signalling mechanism requires that the insulin receptor act as a tyrosine kinase to phosphorylate tyrosine residues on key protein substrates.

BWA1433 was administered as previously described, in a suspension of 7 mg/ml methyl cellulose containing 10 mg/ml BWA1433. BWA1433 was supplied as a free acid from Glaxo-Wellcome but was adjusted to pH 8.0 with NaOH prior to use. In this way, treated animals were given 12 mg/kg BWA1433 every 12 hours (±1 hour) for one week.

Blood glucose was measured using a One Touch II Glucometer. Serum insulin was measured using a radioimmunoassay kit from Diagnostic Products, and protein concentration was determined using a Bio-Rad kit, both according to manufacturer's instructions.

Partial Purification of Insulin Receptors From Skeletal Muscle

Insulin receptors were prepared from 100 mg frozen powdered skeletal muscle using lectin affinity chromatography, as taught by Caro, *J. Clin. Invest.*, 79:1330–1337 (1987). Supernatants from detergent (Triton X-100) solubilized muscle were cycled over 0.3 ml bed volume wheat germ agglutinin agarose (WGA) columns, after which the columns were washed thoroughly overnight. The receptors were eluted in one ml of buffer containing 25 mM N-[2-hydroxyethyl]piperazine-N'-[2-ethanesulfonic acid] (HEPES) (pH 7.6), 55 mM NaCl, 11.25 mM KCl, 0.5 mM $CaCl_2$, 0.5 mM $MgCl_2$, 0.5 mM $Na_3VO_4$, 5 mM NaF, 10% glycerol, 0.05% Triton X-100, and 300 mM-acetyl-D-glucosamine. WGA column eluates were aliquoted to avoid multiple freezing/thawing and were stored at −70° C. until use. Columns were thoroughly washed (50–100 bed volumes wash buffer) and reused. Receptors were quantitated by assaying protein and immunoblotting to specifically assess insulin receptor protein.

Insulin Receptor Kinase Assay

Insulin receptor kinase activity was determined using a modification of previously published techniques by Debant, et al., *Am. J. Physiol.*, 15: E273–E278 (1987) and Handberg, et al., *Diabetologia*, 36:668–674. Briefly, samples of partially purified insulin receptors were incubated for 15 min. at 25° C. with and without insulin in a buffer containing 50 mM HEPES, 0.1 mg/ml BSA, and 0.1% Triton X-100. Then 100 µM [$^{32}$P]-ATP (1.6 $C_i$/mmol), 2 mM $MnCl_2$, 1 mM $MgCl_2$, were added to the incubations and 15 min. later poly Glu:Tyr$_{(4:1)}$ was added and samples incubated for an additional 30 min. The phosphorylated product was applied to filter paper and washed with 10% trichloroacetic acid. Papers were blotted, oven-dried, and radioactivity determined by scintillation counting using a Beckman Model LS3801 scintillation counter. Activity was calculated in mUnits receptor kinase/mg of WGA eluate protein. One unit of activity was defined as the amount of enzyme which incorporates 1 nmole [$^{32}$P]-phosphate into synthetic substrate (poly Glu:Tyr$_{4:1}$) per minute. Subsequent immunoblotting with insulin receptor antibody indicated that the amount of receptor per mg protein was constant within 10–15% in the different preparations. No significant differences between lean and obese muscles were observed in insulin receptor β-subunit immunoreactivity per mg WGA eluate protein.

Sodium Dodecyl Sulfate-polyacrylanide Gel Electrophoresis (SDS-PAGE) and Immunoblotting SDS-PAGE was performed according to Laemmeli, et al., *Nature*, 227, 680–685 (1970). Ten percent SDS gels were used and samples were electrophoresed at 40 mA/gel. Sample buffer consisted of 62.5 mM tris[hydroxymethyl] amino methane (Tris) Cl (Ph 6.8), 2% SDS, 10% glycerol (v/v), 0.2 M dithiothreitol (DTT) and 0.02% bromophenol blue. Transfer of SDS gels to PVDF membranes was performed overnight at 14 volts in 25 mM Tris, 10% methanol, and 192 mM glycine. Membranes were blocked for nonspecific binding by incubating in blocking buffer, tris buffered saline containing Tween® (TBS/T)m, containing 5% nonfat dry milk, or 5% BSA for phosphotyrosine for 1 h at room temperature, or overnight at 4° C. Primary antibody incubations were carried out for 1 h at room temperature at the appropriate dilution in TBS/T+3% milk (or TBS containing 1% BSA in the case of phosphotyrosine). Appropriate dilutions for antibodies were 1:1000, anti-phosphotyrosine (Transduction Laboratories) and 1:1000, anti-PTPase 1B (Upstate Biotechnology, Lake Placid, N.Y.). Membranes were washed twice for 15 min in TBS/T prior to probing with horseradish peroxidase-conjugated secondary antibodies (anti-rabbit or anti-mouse IgG) at a dilution of 1:4000 for 30–60 min at room temperature. Membranes were then washed three times in TBS/T for 15 min and were developed with enhanced chemiluminescence detection reagents (Amersham, Arlington Heights, Ill.). After exposure to Kodak X-AR film, the density of bands were quantitated after scanning using the NIH quantitation program.

Skeletal Muscle Plasma Membranes

Skeletal muscle cytosolic and particulate fractions were prepared using an adaptation of the method of Schmitz, et al., *Acta Diabetologia*, 31:31–36 (1994). Approximately 100 mg frozen tissue were homogenized in 5 ml buffer containing 10 mM $NaHCO_3$, (pH 7.4), 250 mM sucrose, 0.1 mg/ml aprotinin, 0.05 mg/ml leupeptin, 1 mM phenylmethysulfonyl fluoride (PMSF), and 5 mM $NaN_3$ (CHB buffer) and then sonicated for 1 min on ice with three 20-sec bursts. The sonicate was centrifuged at 1,200 g for 10 min at 4° C. Three ml of CHB medium was added to the pellet which was then rehomogenized for 1 min and respun. The suspensions of the two pellets were combined, rehomogenized, and respun at 10,000 g for 10 minutes at 4° C. The 10,000 g pellet was discarded and the supernatant was transferred to a cold Ti75 ultracentrifuge tube and spun at 270,000 g for 90 minutes. The supernatant of the high speed centrifugation (cytosol) was used for PTPase assays. The 270,000 g pellet was resuspended in 0.500 ml buffer containing 250 mM sucrose, 20 mM HEPES (pH 7.4), 0.6 M KCl, and 1% Triton X-100. A 27 gauge syringe needle was used to completely solubilize the pellet. The supernatant was spun at 12,000 rpm for 20 min and the resulting supernatant, termed particulate fraction was then dialyzed overnight at 4° C. against 20 mM HEPES (pH 7.2) and 0.1% β-mercaptoethanol. Samples were stored at −70° C. until used for PTPase assays.

Assays of Protein Tyrosine Phosphatase

Assays were performed at 25° C. using a slight modification of a protocol described by Ahmad and Goldstein, *Am. J. Physiol.*, 268: E932–E940 (1995). Each tube contained 10 µl [$^{32}$P]tyrosine-phosphorylated myelin basic protein (1×10$^4$ dpm; 2×10$^3$ dpm/pmol), 10 µl 5X PTP-ase buffer [250 mM HEPES (pH 7.0), 10 mM EDTA, 5 mM DTT], and 1–5 µg muscle fraction protein and water in a total volume of 40 µl. Consumption of substrate (phosphorylated myelin basic protein) was limited to 20%. The reaction was found to be linear at least to the point where 30% of substrate was consumed (data not shown). The assay differs from that of Ahmed and Goldstein in that the amount of phosphorylated substrate (myelin basic protein) was lower and its specific activity higher, similar to the skeletal muscle PTPase assay described by Tanowitz, et al., *Brain Res.*, 712:299–306 (1996).

[$^{32}$P]-phosphotyrosine labelling of myelin basic protein was performed using EGF receptor to phosphorylate myelin basic protein tyrosine residues as described by Damuni, et al., *FEBS Letters*, 362:311–314 (1994). One unit of PTPase activity is defined as the amount of enzyme releasing 1 nmol phosphate/min from myelin basic protein.

PTPase was measured in skeletal muscle cytosolic fractions, particulate fractions, and in partially purified insulin receptors. To assay PTPase activity in partially purified insulin receptors the WGA eluates were dialyzed overnight against 0.1% β-mercaptoethanol and 20 mM HEPES, pH 7.2, to eliminate phosphatase inhibitors. This was performed since sodium vanadate, a potent PTPase inhibitor, is used in the preparation of the insulin receptors. Dialysis to eliminate vanadate increased observed PTPase activity in the eluates 5- to 6-fold. However, PTPase activity of the undialyzed samples was significant despite the residual presence of vanadate in the WGA column eluate. As normally carried out the tyrosine kinase assay of partially purified insulin receptors contains 0.15 mM vanadate in the final incubation with poly Glu:Ty$_{4:l}$. The present data suggests that even in the presence of 0.15 mM vanadate, insulin receptor kinase activities may be influenced by PTPases bound to the insulin receptor.

In-Gel SDS-PAGE Assay of Protein Tyrosine Phosphatase Activity

In-gel assays were carried out as described by Burridge and Nelson, *Anal. Biochem.*, 232:56–64 (1995). The procedure was modified by decreasing the length of autoradiographic exposure to increase sensitivity. $^{32}$P-poly Glu:Tyr$_{4:1}$ substrate was incorporated into the 100% SDS polyacrylamide gel prior to polymerization. WGA eluates which were run on the gels were concentrated on Centricon filters to approximately 2 mg/ml. Aliquots (100 µg) were run on the gels. Gels were washed overnight to remove SDS. The proteins were first fully denatured in 6M guanidine HCl and then, after electrophoresis, renatured by incubation in phosphatase assay buffers containing 0.04% Tween® 40 and high concentrations of dithiothreitol (DTT). Next, the gels were dried and exposed to Kodak X-Omat x-ray film at –70° C. for various times. Clear bands indicated PTPase activity and were measured from their center to the top of the running gel to estimate molecular weight. In some instances, 1 mM sodium vanadate a protein tyrosine phosphatase inhibitor, was added to the buffer. In some experiments, concentrated WGA eluates were treated with the antibody anti-PTPase 1B (5 g) prior to assaying phosphatase activity. The antibody was added to 50 µl concentrated eluate and the sample was incubated for 1 h on a tube vortexer at room temperature. Fifty µl of 50% protein A Agarose were centrifuged in a separate tube at 14,000 g for 30 sec. The supernatant was removed, and at the end of 1 h, the WGA eluate was introduced to the agarose precipitate and vortexing was continued for an additional 30 min. As a control, WGA eluates that were not treated with antibody were also introduced to the gels. The samples were centrifuged and the supernatants transferred to separate tubes. Fifty µl 2X Laemmli sample buffer were added to the supernatants and the pellets and samples were run on $^{32}$P-substrate-containing gels and processed as described.

[$^{32}$P]-Phosphotyrosine Labelling of Myelin Basic Protein and Poly Glu:Tyr$_{4:1}$ Myelin basic protein (MBP) was labelled with $^{32}$P using a modification of the method of Damuni et al. MBP was stored frozen in 125 µl aliquots containing 10 mg protein/ml. An aliquot (1.25 mg protein) was incubated overnight at 25° C. with 50 mM Tris-Cl (pH 7.0), 1 mM benzamidine, 10 mM MgCl$_2$, 2 mM MnCl$_2$, 1 mM PMSF, 1 mM DTT, 10% glycerol, [$^{32}$P]-ATP (2×10$^3$ dpm/pmol), 0.5 µl EGF receptor kinase doman (Stratagene, LaJolla, Calif.), and water in a total volume of 250 µl. The labelling reaction was stopped by the addition of 1 ml ice cold 20% TCA. The mixture was vortexed and centrifuged for 1 mn at 14,000 g. The supernatant was decanted and the pellet was washed and respun 9 more times using 1 ml cold 10% TCA each time. Then the pellet was resuspended in 600 µl resuspension buffer (50 mM Tris-HCl, pH 7.0, 10% glycerol, and 1 mM benzamidine), vortexed, and centrifuged to remove any residual precipitate. Ten µl aliquots of the resuspended pellet were counted in a Beckman scintillation counter and the solution was diluted in resuspension buffer so that the radioactivity was 1×10$^3$ dpm/µl. This substrate was either used immediately or stored at –70° C. for a maximum of 1 week. Phosphoaminoacid analysis to verify exclusive tyrosine phosphorylation was determined as described by Hunter & Seftan, *Proc Natl. Acad. Sci. USA*, 77(3):1311–1315 (1980).

PolyGlu:Tyr$_{4:1}$ was phosphorylated overnight prior to its integration into the SDS gel matrix for the in-gel PTPase assays. The method of labelling was similar to that described for myelin basic protein. The specific radioactivity of ATP in the labelling buffer was 3 mCi/mmol, at a concentration of 1.67 µM.

Statistics

Experimental values were presented as means ± the SEM. The number of animals per group (n) is indicated in the relevant figures and tables. In analyses examining the relationship of two independent groups, the Student's t-test was performed to determine statistical significance. In comparisons of more than two groups with a single control, statistical significance was determined using analysis of variance followed by Newman-Keuls test to determine treatment effect. The threshold of statistical significance was set at p<0.05.

Results of the use of the methods described above are as follows:

Insulin Receptor Kinase Activity of Control and of BW1433-treated Zucker Rats

Defects of the insulin receptor may contribute to the insulin resistance in muscles of obese, hyperinsulinemic rodents. Insulin receptor kinase activities of receptors isolated from muscles of fasted lean and obese Zucker rats, treated and not treated with BWA1433 were measured using poly Glu:Tyr$_{4:1}$ as substrate.

These measurements were designed to determine whether the BWA1433-induced increase in insulin sensitivity previously observed correlates with an improvement in insulin receptor tyrosine kinase activity. BWA1433 (or vehicle)-treated animals were fasted overnight. Two hours after the AM dose of BWA1433, or vehicle, either one international unit human recombinant insulin (Eli Lilly, Indianapolis, Ind.) or saline solution was injected into the saphonous vein superior to its bifurcation. The gastrocnemius was dissected inferiorly and separated from the soleus, maintaining the blood supply from the femoral artery. The muscle was retracted and clamped at the achilles tendon, and at three minutes, the gastrocnemius was freeze-clamped with tongs that had been chilled in liquid nitrogen. Insulin receptors from animals given intravenous insulin or saline were partially purified from each of the four groups (lean or obese, ± BWA1433).

Figure 4A:
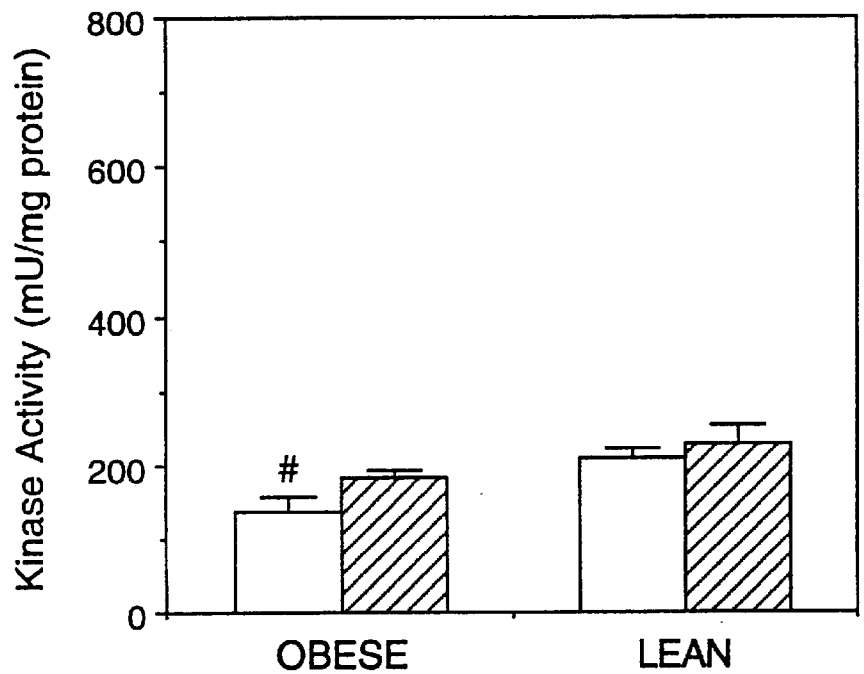
FIG. 4 shows the effect of BWA1433 treatment on insulin receptor kinase activity in gastrocnemius muscle from obese and lean Zucker rats, determined according to the methods of Example 3; panel A shows preparations from rats gives insulin in vivo but not in vitro, and panel B shows the same preparations to which one $\mu$M insulin was added in vitro. Values shown are mean ± SEM, n=6–8 per group, *$p<0.05$ compared to paired control values, #$p<0.05$ compared to paired insulin injected, lean control value.

Insulin receptor kinase activity was measured 1) in the basal state in non-insulin-injected animals, 2) in insulin-injected animals without added insulin, and 3) in receptors isolated from insulin injected animals but stimulated in vitro with 1 µM exogenous insulin. Skeletal muscles from experimental animals not injected with insulin had similar low values of insulin receptor kinase (data not shown). Intravenous insulin-injection increased the observed activity of the insulin receptor kinase 7- to 12-fold when measured in the absence of insulin added in vitro (FIG. 4A). However, the kinase activity was 40% lower in obese control compared to lean control animals. BW1433 treatment induced a small but significant increase in the kinase activity of obese animals.

Figure 4B:
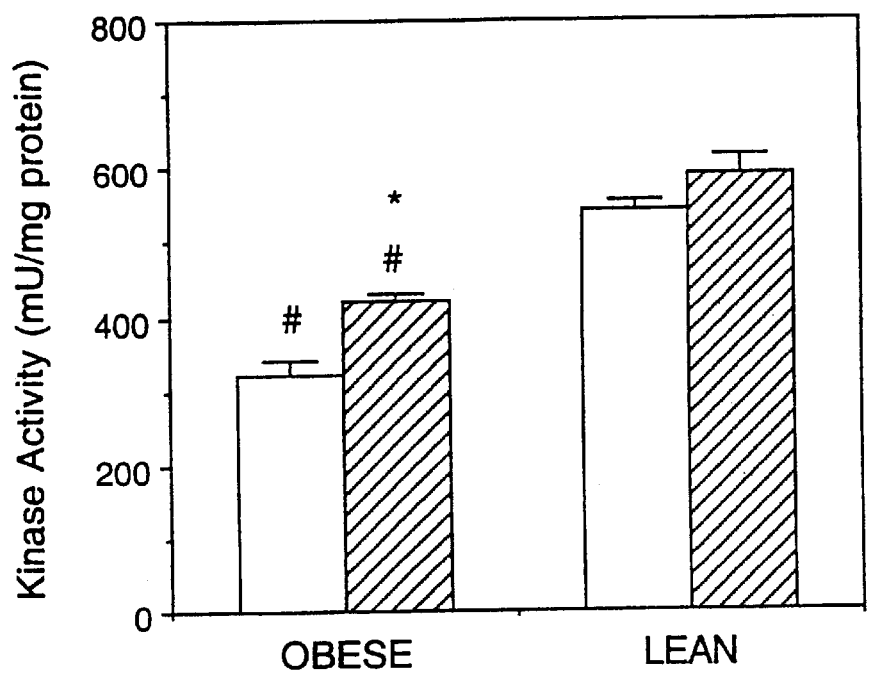

When excess (1 µM) insulin was added to the isolated insulin receptor from animals pretreated with insulin in vivo, the kinase activity increased another 2- to 3-fold. Kinase activities of insulin receptors isolated from muscles of untreated obese animals were 42% lower than the kinase activities isolated from untreated lean animals, as shown in FIG. 4B. BW1433 treatment increased the kinase activities of insulin receptors isolated from obese rats, but had no significant influence on kinases isolated from lean rats.

Protein Tyrosine Phosphatase Activity

Figure 5A:
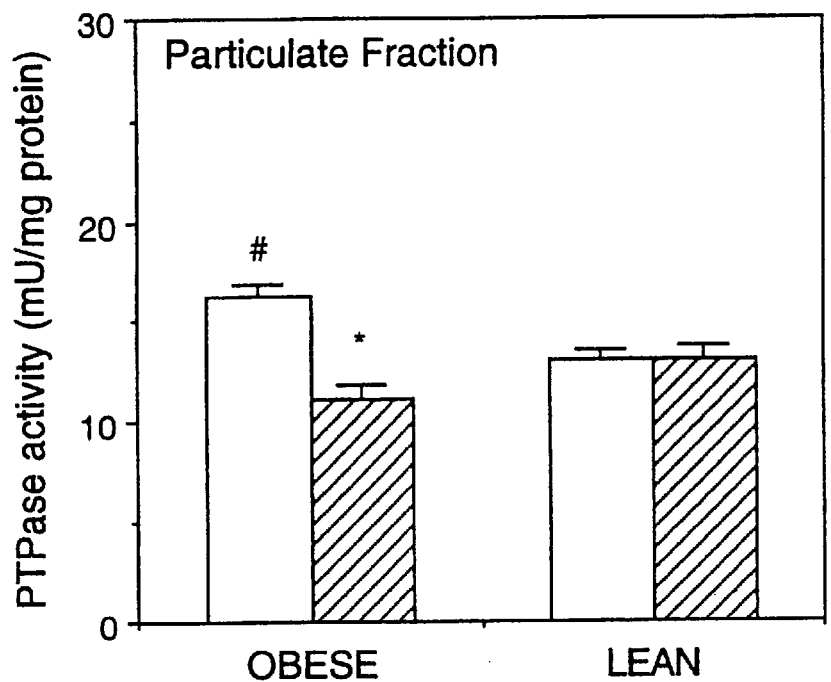
FIG. 5 shows the effect of BWA1433 treatment on phosphotyrosine phosphatase activity in the cytosol and particulate fraction of gastrocnemius from obese and lean Zucker rats, determined according to the methods of Example 3. Values shown are mean ± SEM, n=6–8 per group, *$p<0.05$ compared to paired control values with no BWA1433 treatment, #$p<0.05$ compared to paired control.
Figure 5B:
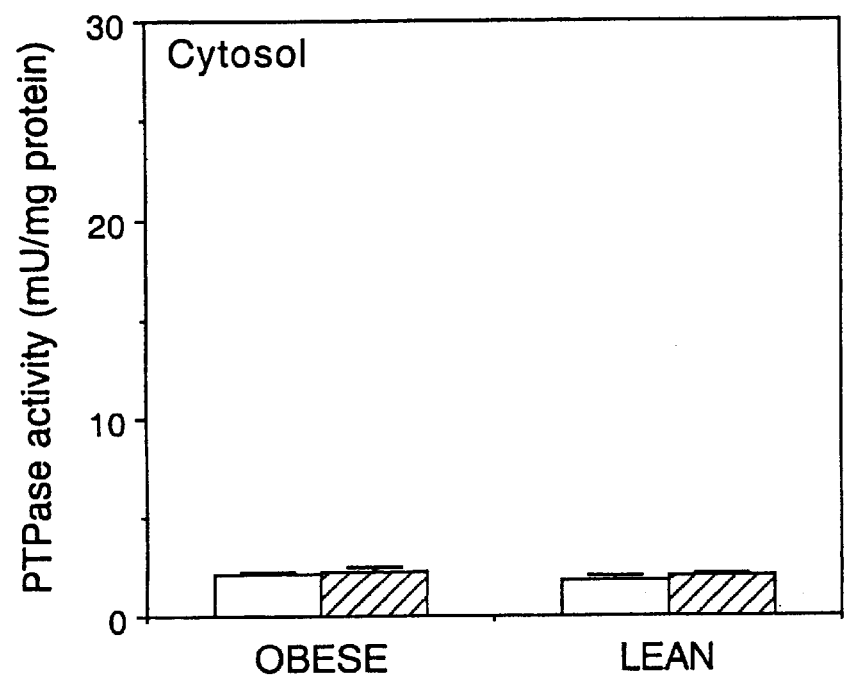

Further experiments were designed to test the hypothesis that excessive activity of protein tyrosine phosphatases (PTPases) may also induce insulin resistance in obese Zucker rats. PTPase activity was measured in the particulate and cytosolic fractions of gastrocnemius obtained from the same animals used in the experiments of FIGS. 4A and 4B. These animals had been injected intravenously with 1 IU of insulin 3 min before the muscles were freeze clamped. 5'-Nucleotidase activity was negligible in cytosolic samples (data not shown) indicating minimal contamination with the plasma membrane fraction. Phosphatase activity per mg protein in the particulate fraction averaged 9-fold higher than that fund in the cytosol, as shown in FIG. 5A, versus FIG. 5B. No differences between groups were observed in the low phosphatase activity found in the cytosolic fractions. In contrast, in the particulate fractions, PTPase activity was 25% higher in samples from obese controls compared to samples from lean controls. BWA1433 treatment of obese Zucker rats resulted in a reduction of phosphatase activity of lean animals.

Figure 6:
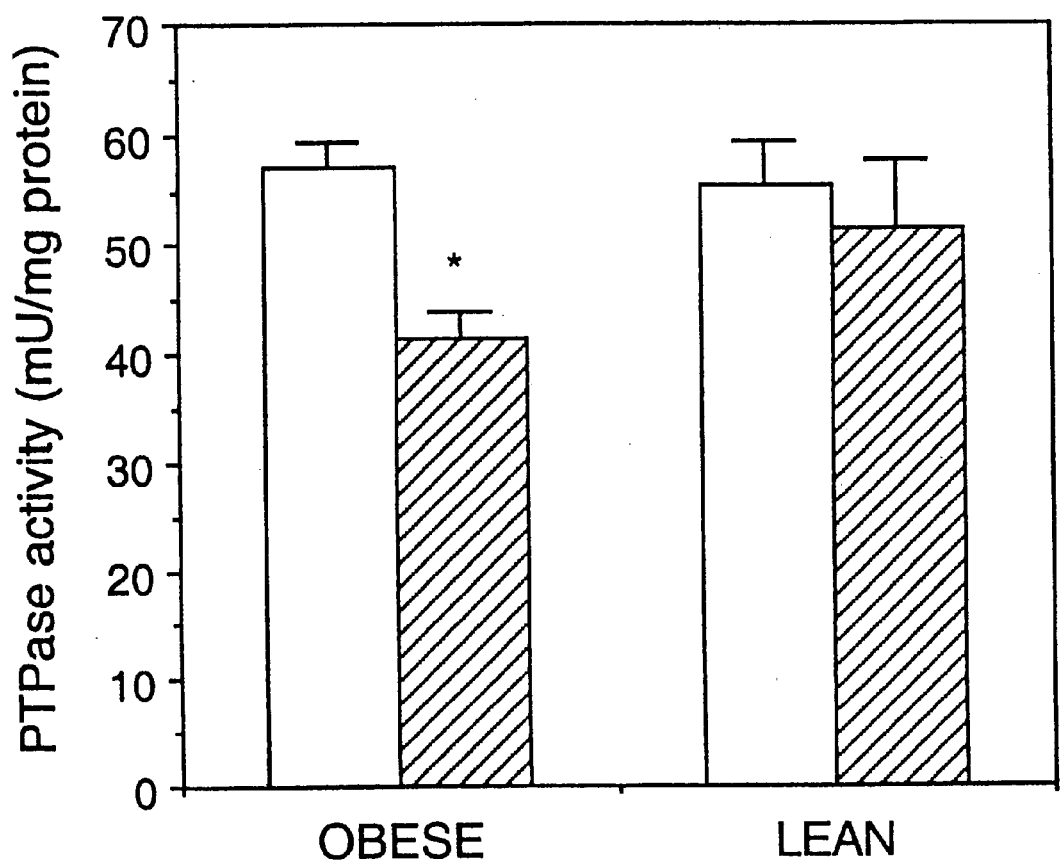
FIG. 6 shows the effect of BWA1433 treatment on phosphotyrosine phosphatase activity in partially-purified insulin receptor preparations of gastrocnermius from obese and lean Zucker rats, determined according to the methods of Example 3. Values shown are mean ± SEM, n=6,*$p<0.05$, compared to corresponding paired control value.

Since a number of protein tyrosine phosphatases are known to associate with the insulin receptor, particularly those having src homology domains, the phosphatase activity was also measured in preparations of partially-purified insulin receptors. Somewhat surprisingly, no significant differences in phosphatase activity of the dialyzed insulin receptors were observed comparing lean and obese control groups (FIG. 6). However, BWA1433 treatment resulted in a 27% reduction of phosphatase activity in obese rats, compared to untreated controls. PTPase activity per mg protein was enriched in WGA eluates, compared to crude muscle particulate fractions or cytosol fractions (3.6 times and 28 times greater, respectively). The in vitro inclusion of 10 $\mu$M BWA1433 in WGA eluates from obese controls had no effect on protein tyrosine phosphatase activity.

Characterization of Protein Tyrosine Phosphatases Which Associate With the Insulin Receptor Antagonist-induced changes in individual PTPases may be larger on a percent basis than the changes observed in total tissue PTPases. Since BWA1433 was found to modulate PTPase activity in insulin receptor preparations from obese rats, an in-gel protein tyrosine phosphatase assay was employed to initiate identification of individual phosphatases in WGA eluates, as taught by Burridge & Nelson, *Anal. Biochem.*, 232:56–64 (1995). When 100 $\mu$g of WGA eluate protein was run on the gels, clear plaques due to the activity of at least 5 different PTPases, as shown in FIG. 7A, were observed. Concentrated wheat germ eluates (~100 $\mu$g) were run on SDS-polyacrylamide gels containing $^{32}$P-poly glu:tyr$_{4:1}$. Following electrophoresis, protein was renatured and assayed for protein tyrosine phosphatase activity. Phosphatases were observed as clear plaques on autoradiographs (FIG. 7A). In some instances, activity was assessed using 1 mM sodium vanadate in the assay buffer (FIG. 7B). Numbers on the left indicate the molecular weights of candidate phosphatases, which were estimated by comparison with molecular weight markers.

Figure 7:
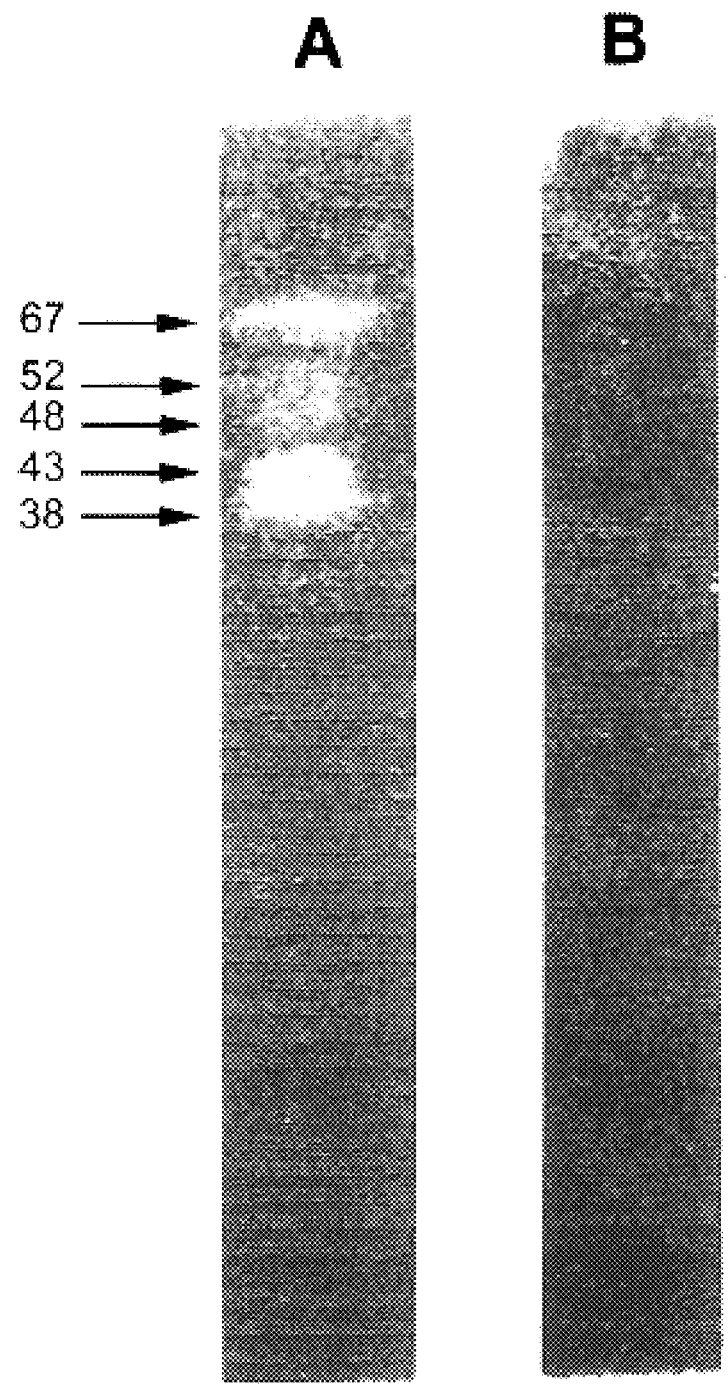
FIG. 7 shows an in-gel protein tyrosine phosphatase assay of concentrated wheat germ agarose eluates, determined according to the methods of Example 3.

To control for presence of protease activity, which might have produced clear plaques, 1 mM sodium vanadate, a potent tyrosine phosphatase inhibitor, was included in the buffers of some gels. Bands disappeared in gels incubated with sodium vanadate (FIG. 7B). Bands also became very faint when DTT was omitted from the incubation buffer since DTT is required to maintain activity of almost all protein tyrosine phosphatases. As shown in FIG. 7, the molecular weights of candidate phosphatases were 67, 52, 48, 43, and 38 kDa. This may be only a partial list of the molecular weights of candidate protein tyrosine phosphatases, since higher molecular weight receptor bound tyrosine phosphatases resist renaturation.

Figure 8:
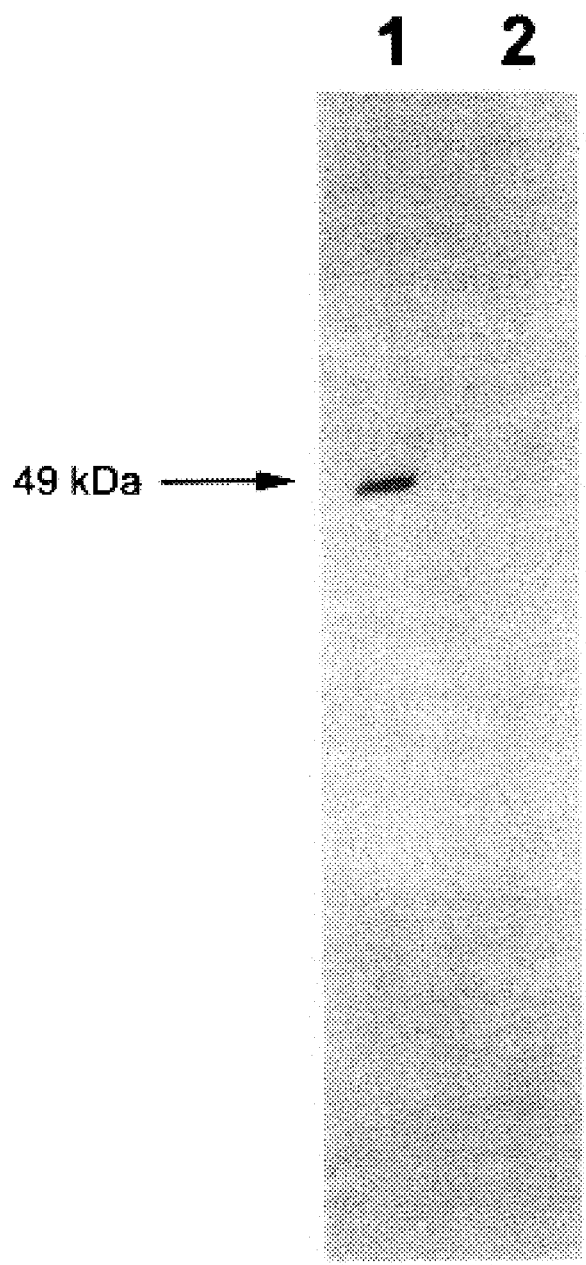
FIG. 8 shows a Western blot of concentrated wheat germ agarose eluates with anti-PTPase 1B using 10% SDS-polyacrylamate gels, determined according to the methods of Example 3.

The protein tyrosine phosphatase, PTPase 1B has been previously characterized as a 50 kDa protein that undergoes a C-terminal truncation to yield a 37.5 kDa protein which binds to the insulin receptor. To test the possibility that the 38 and 48 kDa bands may be due to PTPase 1B activity, a monoclonal antibody to the N-termninal portion of human PTPase 1B was used identify the protein (FIG. 8). The A-431 cell lysate containing PTPase 1B was run as a positive control in lane 1. Concentrated wheat germ eluate (~100 $\mu$g) was run in lane 2, also on 10% SDS-polyacrylamide gels. Following electrophoresis, proteins are transferred to PVDF membranes. PTPase 1B was detected by blotting with PTPase 1B antibodies, and then with horseradish-peroxidase linked antimouse antibodies, and developed using enhanced chemiluminescence. A 49 kDa band was detected in the lane containing the positive control for PTPase 1B. However, no bands were detected in the WGA eluate lane. Longer duration of exposure (up to 30 min) did not yield any bands in the WGA lane.

Figure 9:
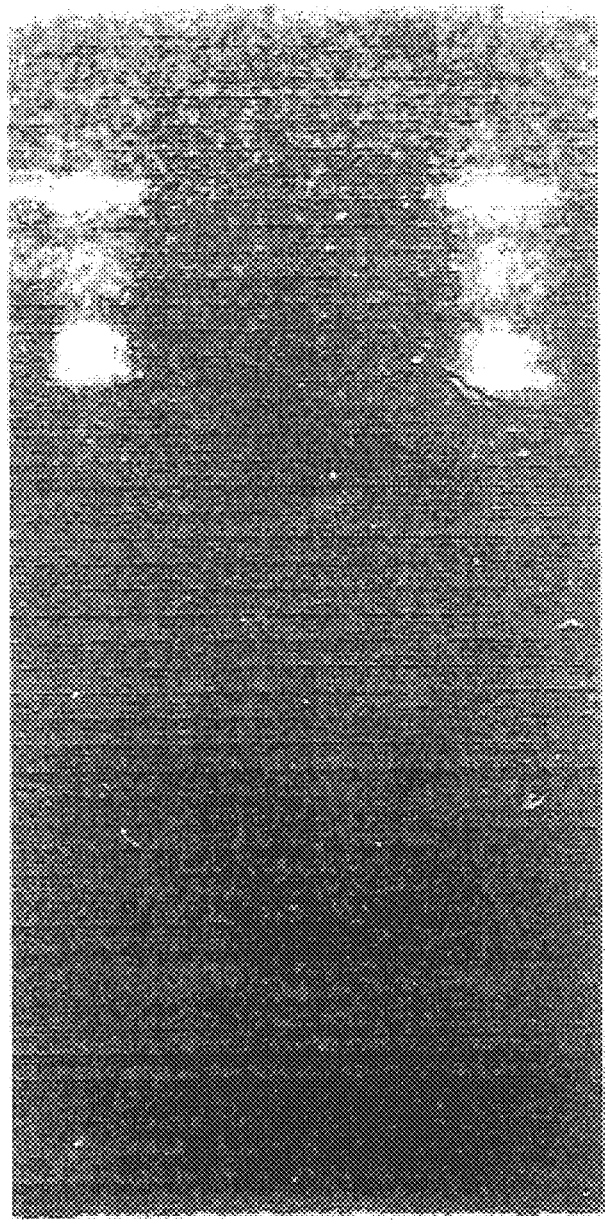
FIG. 9 shows an in-gel protein tyrosine phosphatase assay of concentrated wheat germ agarose eluates after immuno-precipitation with antibodies to PTPase 1B, determined according to the methods of Example 3.

As an additional test for the presence of PTPase 1B, the in-gel assay was performed as before, but prior to electrophoresis, the WGA eluates were either treated or untreated with the PTPase 1B antibody linked to protein A Agarose in order to immunoprecipitate PTPase 1B from the eluates. After immunoprecipitation, the untreated eluates, the supernatant from the immunoprecipitation, and immunoprecipitates, were run on the in-gel assay. The antibody did not remove appreciable phosphatase activity from the WGA eluates, as shown in FIG. 9, lane 2. Moreover, PTP-ase activity in the supernatants closely resembled the activity of the untreated eluates, as shown in FIG. 9, lanes 1 vs. 3. Concentrated wheat germ eluates (~100 $\mu$g) were run on SDS-polyacrylamide gels containing [$^{32}$P]-poly glu:tyr$_{4:1}$. Following electrophoresis, proteins were renatured and assayed for protein tyrosine phosphatase activity. Lane 1: Untreated WGA eluates, Lane 2: Anti-PTPase 1B-protein A agarose precipitate, Lane 3: Supernatant from immunoprecipitation.

Oral administration of BWA1433, an adenosine receptor antagonist, to obese rats improves the in vivo capacity of insulin to stimulate glucose disposal. Moreover, Example 2 demonstrates that the influence of the antagonist is tissue selective. That is, under in vivo conditions, it stimulates insulin-dependent glucose uptake in skeletal muscle, but impairs insulin-mediated glucose uptake in adipose tissue. The present example helps to define the nature of the skeletal muscle insulin resistance in obese Zucker rats and elucidates how the muscle $A_{2B}$ adenosine receptor activity impacts specifically on skeletal muscle insulin sensitivity in these animals.

Higher than normal PTPase activity in skeletal muscle of obese Zucker rats has been reported, as has the increase of PTPase in skeletal muscle tissue of insulin resistant human subjects. The present example shows that the decrease in total muscle PTPase activity in response to $A_{2B}$ adenosine receptor is responsible for the improvement in insulin sensitivity; this conclusion is strengthened by the observation that the PTPase activity is concentrated in a membrane fraction that co-eluates with the insulin receptor, and the insulin receptor associated PTPase concentration is lowered by systemic adenosine receptor antagonism. However, a smaller fraction of the total particulate PTPase associates with the insulin receptor in obese compared to lean rats. Some PTPases associate with the insulin receptor only after the receptor is tyrosine phosphorylated, and the fact that the kinase activity of receptors from obese animals is 40–50% lower than that of lean animals may account for the observation that the PTPase per mg protein is not elevated in obese compared to lean partially purified insulin receptors. If one calculates units of PTPase activity/units tyrosine kinase activity, the ratio is almost twice as high in obese compared to lean WGA fractions. The observation that the BWA1433-induced-decrease in PTPases occurs only in obese animals that exhibit elevated total particulate PTPase supports the hypothesis that elevated PTPase contributes to the insulin resistance of obese rats.

The data confirm the presence of crosstalk between the G-protein linked adenosine receptor and the insulin signaling pathway, and that the crosstalk is mediated at least in part by regulation of PTPases. This example shows that $A_{2B}$ adenosine receptors in muscle acting through $G_q$ heterotrimeric GTP binding proteins may increase PTPase activity, as demonstrated above; this upregulation of PTPase activity may be an important site of skeletal muscle insulin resistance. The administration of $A_{2B}$ adenosine receptor antagonist by blocking the increase in PTPases will therefore increase insulin sensitivity.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for improving insulin sensitivity in a patient comprising:
   administering to said patient an effective amount of at least one $A_{2B}$ adenosine receptor antagonist, or a pharmaceutically acceptable salt or solvate thereof.

2. The method of claim 1, wherein said patient has non-insulin dependent diabetes mellitus.

3. The method of claim 1, wherein said patient is pre-diabetic.

4. The method of claim 1, wherein said patient has impaired glucose tolerance.

5. The method of claim 1, wherein said $A_{2B}$ adenosine receptor antagonist, salt or solvate thereof is contained in a suitable pharmaceutical carrier.

6. The method of claim 5, wherein said suitable pharmaceutical carrier is selected from the group comprising a liquid carrier and a solid carrier.

7. The method of claim 1, wherein said method of administration is oral, parenteral or rectal.

8. The method of claim 7, wherein administration is oral.

9. The method of claim 1, wherein said effective amount of said antagonist is enough to achieve blood concentrations of at least ten times the binding constant for the antagonist.

10. The method of claim 1, wherein said $A_{2B}$ adenosine receptor antagonist is a xanthine derivative.

11. The method of claim 10, wherein said xanthine derivative is selected from the group comprising 3-n-propylxanthine, 1,3-dipropyl-8-(p-acrylic)phenylxanthine, 1,3-dipropyl-8-cyclopentylxanthine, 1,3-dipropyl-8-p-sulfophenyl)xanthine, xanthine amine congener, and 1,3-dipropyl-8-[2-(5,6-epoxynorbonyl] xanthine.

12. The method of claim 10, wherein said xanthine derivative is 1,3-dimethylcyclohexyl-8-phenyl(4-acrylate)-xanthine.

13. A method for stimulating glucose uptake in the muscle of a patient comprising:
   administering to said patient an effective amount of at least one $A_{2B}$ adenosine receptor antagonist, or a pharmaceutically acceptable salt or solvate thereof.

14. The method of claim 13, wherein said $A_{2B}$ adenosine receptor antagonist, salt or solvate thereof is contained in a suitable pharmaceutical carrier.

15. The method of claim 13, wherein said $A_{2B}$ adenosine receptor antagonist is a xanthine derivative.

* * * * *